US010810239B2

(12) United States Patent
Kimura

(10) Patent No.: US 10,810,239 B2
(45) Date of Patent: Oct. 20, 2020

(54) SEQUENCE DATA ANALYZER, DNA ANALYSIS SYSTEM AND SEQUENCE DATA ANALYSIS METHOD

(71) Applicant: Hitachi High-Tech Corporation, Minato-ku, Tokyo (JP)

(72) Inventor: Kouichi Kimura, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 398 days.

(21) Appl. No.: 15/301,086

(22) PCT Filed: Mar. 12, 2015

(86) PCT No.: PCT/JP2015/057348
§ 371 (c)(1),
(2) Date: Sep. 30, 2016

(87) PCT Pub. No.: WO2015/151758
PCT Pub. Date: Oct. 8, 2015

(65) Prior Publication Data
US 2017/0017717 A1    Jan. 19, 2017

(30) Foreign Application Priority Data
Apr. 3, 2014   (JP) ................. 2014-077278

(51) Int. Cl.
*G06F 16/33* (2019.01)
*G16B 30/00* (2019.01)

(52) U.S. Cl.
CPC ........... *G06F 16/334* (2019.01); *G16B 30/00* (2019.02)

(58) Field of Classification Search
None
See application file for complete search history.

(56) References Cited

U.S. PATENT DOCUMENTS

| 2006/0281097 A1 | 12/2006 | Chiu et al. |
| 2013/0331277 A1 | 12/2013 | Van Eijk |
| 2015/0363549 A1 | 12/2015 | Kimura |

FOREIGN PATENT DOCUMENTS

| JP | 2008-547080 A | 12/2008 |
| JP | 2009-116559 A | 5/2009 |
| JP | 2014-502513 A | 2/2014 |
| WO | WO 2014/132497 A1 | 9/2014 |

OTHER PUBLICATIONS

Shendure et al. Next-generation DNA sequencing Nature Biotechnology vol. 26, pp. 1135-1145 (Year: 2008).*
Zhang et al. Zoom Lite: next-generation sequencing data mapping and visualization software Nucleic Acids Research vol. 38, pp. W743-W748 (Year: 2010).*
Goecks et al. Galaxy: a comprehensive approach for supporting accessible, reproducible, and transparent computational research in the life sciences Genome Biology vol. 11, article R86 (Year: 2010).*
Xu et al. SAMMate: a GUI tool for processing short read alignments in SAM/BAM format Source Code for Biology and Medicine vol. 6, article 2 (Year: 2011).*
International Search Report (PCT/ISA/210) issued in PCT Application No. PCT/JP2015/057348 dated Jun. 2, 2015 with English translation (5 pages).
Japanese-language Written Opinion (PCT/ISA/237) issued in PCT Application No. PCT/JP2015/057348 dated Jun. 2, 2015 (3 pages).
Li, Heng et al. "The Sequence Alignment/ Map Format and SAMtools", Bioinformatics, vol. 25, No. 16, 2009, pp. 2078-2079.
Li, Heng et al. "Fast and Accurate Short Read Alignment with Burrows-Wheeler Transform", Bioformatics, Vo. 25, No. 14, 2009, pp. 1754-1760.
Depristo, Mark A. et al, "A Framework for Variation Discovery and Genotyping Using Next-Generation DNA Sequencing Data", Nature Genetics, vol. 43, No. 5, May 2011, pp. 491-501.
Kimura, Kouichi et al., "A New Approach to DNA Sequence Variation Analysis Using Burrows-Wheeler Transform of Massive Short-Read Data", Proceedings of Advances in Genome Biology & Technology Conference (AGBT), 2013, Marco Island, p. 202.
Kimura, Kouichi et al., "Computation of rank and Select Functions on Hierarchical Binary String and Its Application to Genome Mapping Problems for Short-Read Sequences", Journal of Computational Biology, vol. 16, No. 11, 2009, Mary Ann Liebert Inc., pp. 1601-1613.
Ferragina, Paolo et al., "Opportunistic Data Structures With Applications", $41^{st}$ IEEE Symposium of Foundations of Computer Sciences, FOCS, 2000, pp. 1-15 (16 total).
Kimura, Kouichi et al., "Localized Suffix Array and Its Application to Genome Mapping Problems for Paired-End Short Reads", Genome Informatics, 2009, vol. 23, No. 1, pp. 60-71.

* cited by examiner

*Primary Examiner* — John S Brusca
(74) *Attorney, Agent, or Firm* — Crowell & Moring LLP

(57) ABSTRACT

A sequence data analyzer comprising: a read dictionary preparation unit creating a read sequence dictionary based on a concatenation string, the concatenation string constituted of a pair of a left sequence and a right sequence, which are obtained by sequencing a sample DNA fragment respectively from the left and right ends, and connecting characters connecting these sequences together; and a sample reconstruction unit extracting, as a sample sequence, a string up to a terminal character positioned in the string of a hit position of a query sequence in the read sequence dictionary, and extracting, as a mate sequence, the left sequence or right sequence until the appearance of a terminal character on the side where the hit position doesn't exist in the sample sequence.

12 Claims, 9 Drawing Sheets

FIG.7A
| CHROMOSOME NAME | BASE POSITION COORDINATE | NORMAL BASE KIND | MUTATED BASE KIND |
|---|---|---|---|
| chr7 | 123,456 | A | G |
| chrX | 345,678 | C | T |
| ... | | | |
FIG.7B
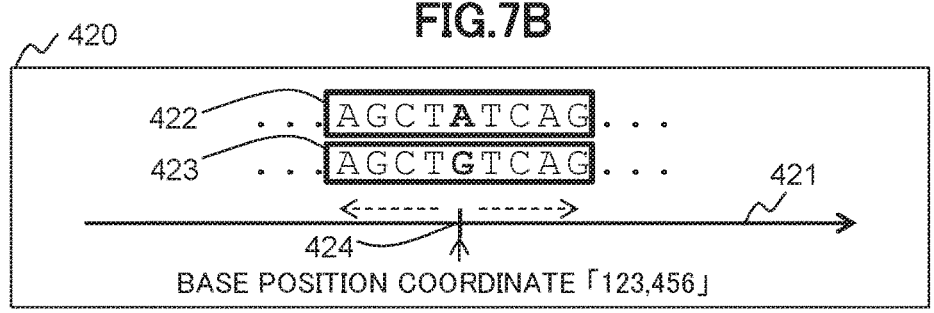
FIG.7C
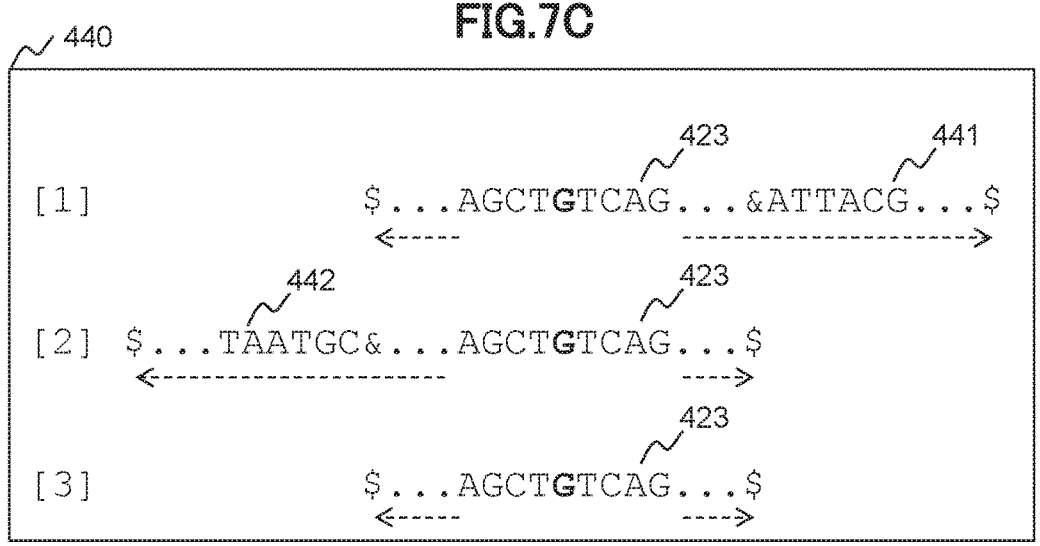
FIG.7D
| CHROMOSOME NAME | BASE POSITION COORDINATE | NORMAL BASE KIND | MUTATED BASE KIND | NUMBER OF DETECTED NORMAL BASES | NUMBER OF DETECTED MUTATED BASES |
|---|---|---|---|---|---|
| chr7 | 123,456 | A | G | 23 | 19 |
| chrX | 345,678 | C | T | 43 | 0 |
| ... | | | | | |

FIG.9A
| CHROMOSOME NAME | BASE POSITION COORDINATE | MUTATION TYPE | MUTATION LENGTH |
|---|---|---|---|
| chr3 | 654,321 | DELETION | 500BASES |
| chr12 | 111,222 | INSERTION | 100BASES |
| ... | | | |
FIG.9B
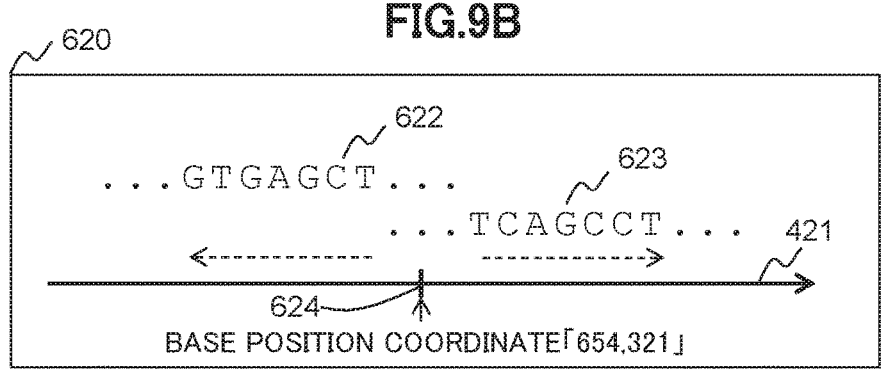
FIG.9C
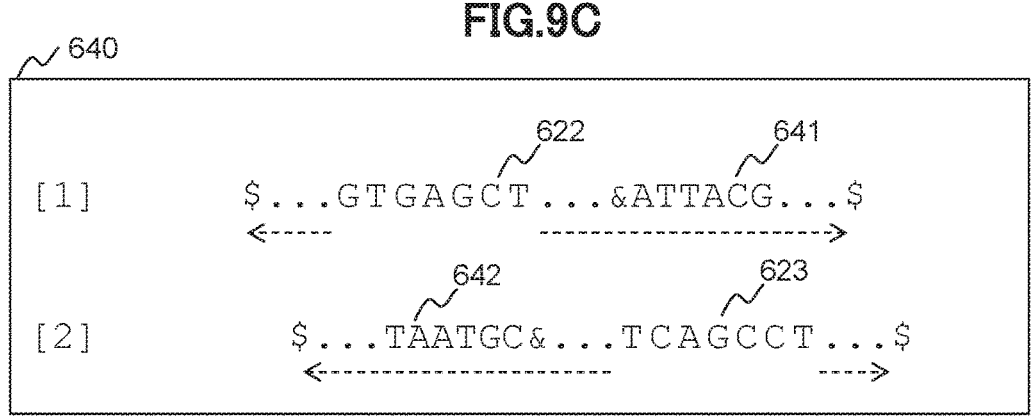
FIG.9D
| CHROMOSOME NAME | BASE POSITION COORDINATE | MUTATION TYPE | MUTATION LENGTH | DETECTION NUMBER OF PRESENCE OF MUTATIONS | DETECTION NUMBER OF ABSENCE OF MUTATIONS |
|---|---|---|---|---|---|
| chr3 | 654,321 | DELETION | 200BASES | 31 | 29 |
| chr12 | 111,222 | INSERTION | 50BASES | 57 | 0 |
| ... | | | | | |

SEQUENCE DATA ANALYZER, DNA ANALYSIS SYSTEM AND SEQUENCE DATA ANALYSIS METHOD

CROSS-REFERENCE TO RELATED APPLICATIONS

The present application claims priority under 35 U.S.C § 119 to Japanese patent Application No. 2014-77278, filed on Apr. 3, 2014, entitled "SEQUENCE DATA ANALYZER, DNA ANALYSIS SYSTEM AND SEQUENCE DATA ANALYSIS METHOD". The contents of this application are incorporated herein by reference in their entirely.

BACKGROUND OF THE INVENTION

Field of the Invention

The present invention relates to a sequence data analyzer, a DNA analysis system and a sequence data analysis method.

Discussion of the Background

The base sequence of a genome DNA has already been sequenced as a whole, and the base strings are disclosed mainly on servers connected to the Internet. Researchers perform a collation (genome mapping) of base positions between sample DNA fragments of a subject sequenced by a sequencer and the genome DNA as a model (reference data) to detect mutations in the sample DNA. Mutation is, for example, a different part, for example, Single Nucleotide Polymorphism (SNP) and Structure Mutation (SV) between a base string of a genome DNA and a base string of a sample DNA fragment. Additionally, a sample DNA fragment is obtained by performing a fragmentation processing on a piece of sample DNA in a sequencer.

Here, since the sequencer can only sequence a limited length of a DNA sequence, a paired-end method of handling two pieces of (paired) read sequences obtained by sequencing a limited length (only a part of a sample DNA fragment) from each of both ends of sample DNA fragments aligned substantially uniform in length is known. In other words, in a paired-end method there is a section belonging to neither of paired read sequences not to be sequenced in the center of a sample DNA fragment. Accordingly, in genome mapping of a paired read sequence sequenced by a paired-end method at a base position in a genome DNA, it is possible to map a piece of a sample DNA fragment in a genome DNA with high accuracy by position mapping together with the other read sequence rather than by position mapping of only one read sequence of a pair.

Since the data amount of base strings of a genome DNA and a sample DNA fragments are enormous, when two pieces of (paired) read sequences are mapped in a genome DNA by a paired-end method as described above, processing efficiency and data compression are required. Thus, the various technologies for enhancing efficiency in genome mapping have been proposed as described below.

The paired-end diTag in which the sequence heading from 5' terminal to 3' terminal on a full length cDNA is maintained is sequenced in genome-wide transcriptome profiling, and a method of detecting efficiently diTag sequences adjacent to a specified spacer sequence is known (Patent Literature 1).

In order that the enormous amount of short reads generated by a new DNA sequencer is aligned with a reference genome sequence fast and accurately, the technology of performing a BW (Burrows-Wheeler) transformation on a genome sequence and of identifying fast the position at which the sequence corresponding to the leading several tens seed sequence of a short read appears in a reference genome is generally and widely used (for example, non patent document 1).

Further, in order to reduce ambiguities that there are a plurality of possible positions to be aligned in this case, a paired short read mapping also has been widely performed (for example, non Patent Literature 2). Normally, the same name (for example, QNAME in non Patent Literature 1) is given to 2 short reads to indicate they are paired.

A method of using the large amount of data obtained by mapping a large amount of short reads on a reference genome is generally and widely used for performing a mutation analysis (for example, non Patent Literature 3). Further, in order to perform a mutation analysis without performing the mapping computation requiring a high computational cost, there is a possible approach of using the BW transformations on reference genome sequence and short read sequences (Patent Literature 2, non Patent Literature 4).

Non Patent Literature

Patent Literature 1: Japanese Unexamined Patent Application Publication No. 2008-547080
Patent Literature 2: Japanese Unexamined Patent Application No. 2013-038919
Non Patent Literature 1: Li H., Handsaker B., Wysoker A., Fennell T., Ruan J., Homer N., Marth G., Abecasis G., Durbin R. and 1000 Genome Project Data Processing Subgroup: The Sequence alignment/map (SAM) format and SAMtools. Bioinformatics, 25, 2078-9 (2009).
Non Patent Literature 2: Li H. and Durbin R. Fast and accurate short read alignment with Burrows-Wheeler Transform. Bioinformatics, 25:1754-60 (2009).
Non Patent Literature 3: M. A. DePristo, et al., A framework for variation discovery and genotyping using next-generation DNA sequencing data. Nature Genetics 43(5): 491-498 (2011).
Non Patent Literature 4: K. Kimura and A. Koike: A new approach to DNA sequence variation analysis using Burrows-Wheeler transform of massive short-read data, in Proceedings of Advances in Genome Biology & Technology Conference (AGBT) 2013, Marco Island, p. 202.

SUMMARY OF THE INVENTION

Problems to be Solved by the Invention

In order to handle in a computer the pair information on a the large amount of read sequence data sequenced by a paired-end method, the identifiers (pointer information) to link one read sequences of a pair to the other read sequences of a pair are required. These identifiers require multiple bits to identify a pairing partner uniquely. This increases the data sizes of the identifiers to be a cause of deterioration in computing efficiency. For example, when there are 8 billion pieces of short reads having 100 bases in length, 4 billion patterns of identifiers are required. Since each identifier requires 4 bytes at least, the data size of identifiers for all reads reaches up to 4 GB (gigabyte).

To this end, the present invention is to efficiently find out one read sequence from the other read sequence, both of which constitute a pair sequenced from both ends of a sample DNA fragment.

Solution to Problem

In order to solve the forgoing problem, a sequence data analyzer of the present invention comprises a read dictionary preparation unit configured to create for each of sample DNA fragments a concatenation string obtained by connecting with a concatenation character a pair of a left sequence and a right sequence both of which are obtained by sequencing the each of sample DNA fragments from the both ends of the each of the sample DNA fragments, and to prepare a read sequence dictionary based on a string obtained by connecting the concatenation strings of the sample DNA fragments with terminal characters;

a query retrieval unit configured to start searching the read sequence dictionary for a hit position being a base character coordinate at which a query sequence generated from a base string of a genome DNA appears;

a sample reconstruction unit configured to start searching the read sequence dictionary for the string from the hit position up to the terminal character positioned on the both sides of the hit position to retrieve the string as a sample sequence, to start searching the sample sequence for the concatenation character positioned on the both sides of the hit position from the hit position, and to extract as a mate sequence from the retrieved concatenation character up to the terminal character on the either the left sequence or the right sequence, where the hit position doesn't exist; and a mapping unit configured to search the genome DNA for a base character coordinate of the base string in which the mate sequence appears.

The other measures will be described as below.

Advantageous Effects of the Invention

According to the present invention, one read sequence can be found out efficiently from the other read sequence, both of which constitute a pair to be sequenced from both ends of a sample DNA fragment.

BRIEF DESCRIPTION OF THE DRAWINGS

The present invention is described in detail below with reference to the attached drawing figures, wherein:

FIG. 5 are explanatory drawings describing a conversion processing of converting to Wavelet Tree form in the processing of creating dictionaries according to an embodiment of the present invention.

FIG. 7 are explanatory drawings showing each data in SNP analysis processing according to an embodiment of the present invention. FIG. 7A shows SNP information. FIG. 7B illustrates query sequences created by the SNP information and a genome sequence dictionary. FIG. 7C illustrates the state in which the query sequence is retrieved from the read sequence dictionary. FIG. 7D shows the analysis results of SNP.

FIG. 9 are explanatory drawings showing each data in the analysis processing of a structural mutation according to an embodiment of the present invention. FIG. 9A shows structural mutation information. FIG. 9B illustrates the query sequences created from the structural mutation information and the genome sequence dictionary. FIG. 9C is the state in which the query sequences are retrieved from the read sequence dictionary. FIG. 9D shows the analysis results of the structural mutations.

DESCRIPTION OF THE EMBODIMENTS

An embodiment of the present invention will now be described in details with reference to the drawings.

Figure 1:
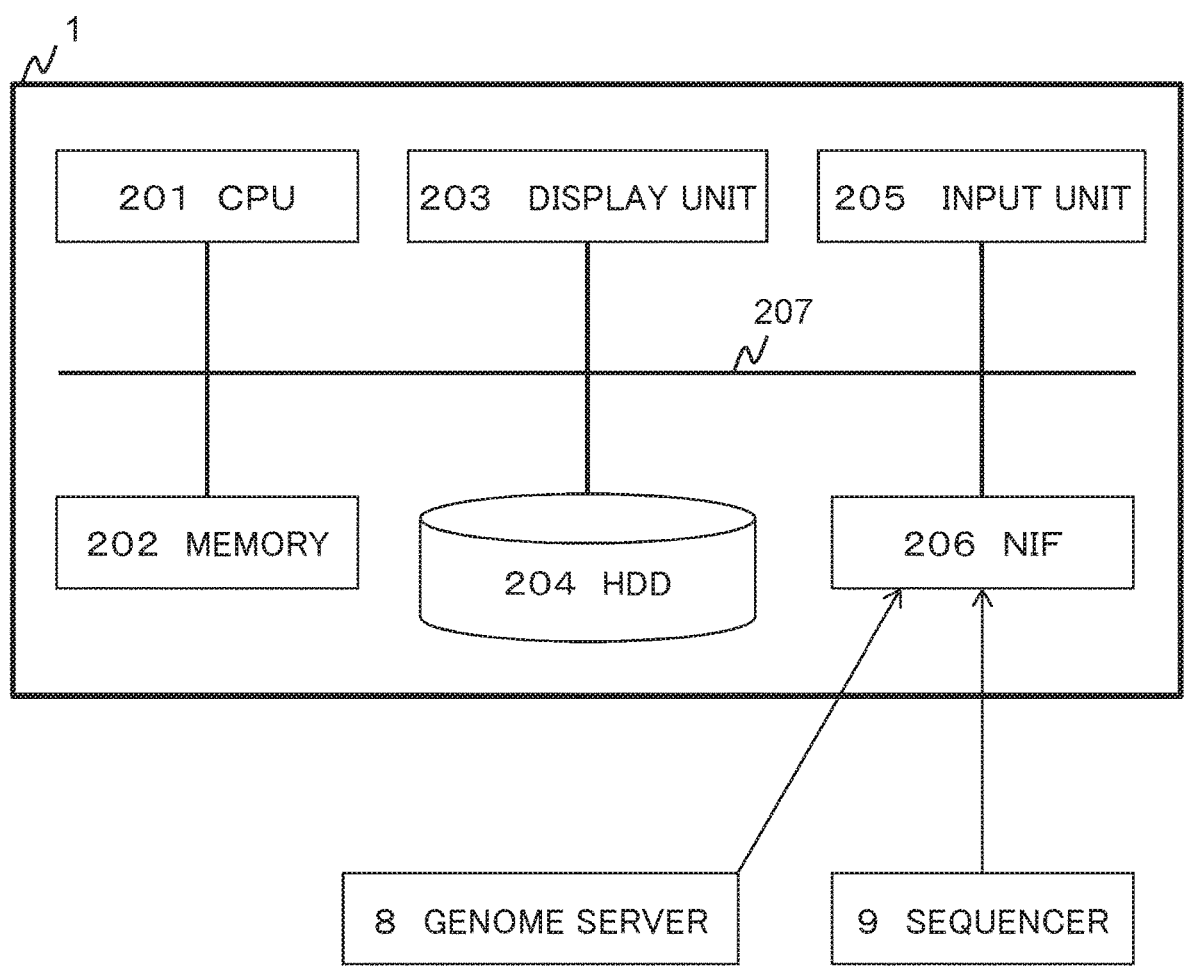
FIG. 1 is a configuration showing a DNA analysis system according to an embodiment of the present invention

FIG. 1 is a configuration showing a DNA analysis system.

A sequence data analyzer 1 is implemented with a computer of a server or the like having a configuration of a conventional computer.

Figure 2:
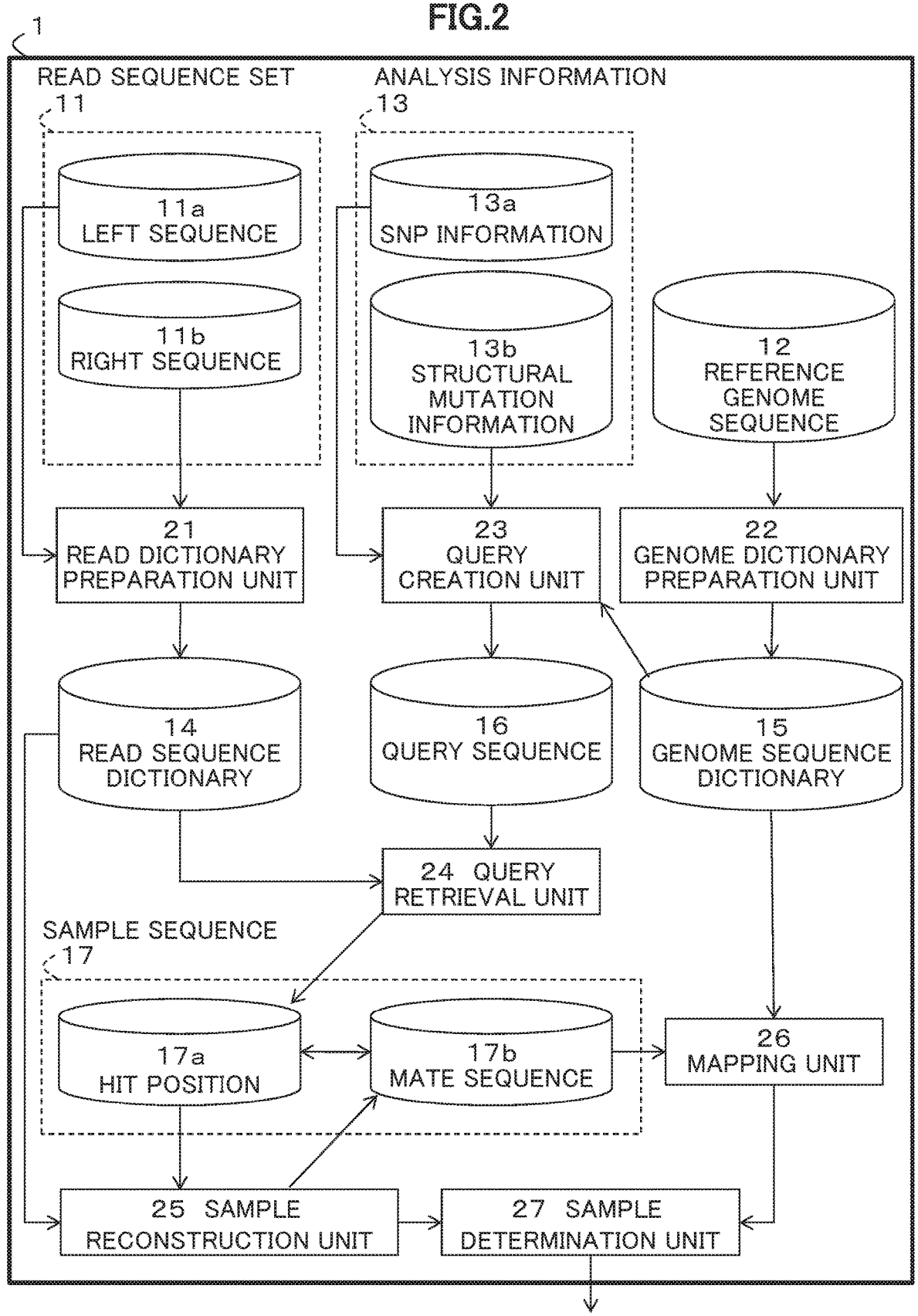
FIG. 2 is a configuration showing a sequence data analyzer according to an embodiment of the present invention

The sequence data analyzer 1 comprises a CPU (Central Processing Unit) 201, a memory 202 being a storage unit in which programs are mainly stored, a GUI (Graphical User Interface) for operation, a display unit 203 for displaying analysis results, a HDD (Hard disk drive) 204 functioning as a storage unit storing sequence dictionaries (a read sequence dictionary 14 and a genome sequence dictionary 15 in FIG. 2) and the like, an input unit 205 of a key board or the like mainly for inputting mutation information such as SNP and parameters, and a Network Interface (NIF) 206 for connecting mainly to the Internet, all of which are connected with a bus 207.

The sequence dictionaries stored in HDD 204 may be stored either in a storage device installed outside of the sequence data analyzer 1 or in a data center or the like through network.

The various flowcharts described in the following are implemented mainly by executing programs of the CPU 201.

The NIF 206 of the sequence data analyzer 1 is connected to a genome server 8 and a sequencer 9 through network.

The sequencer 9 sequences a pair of sequences at both ends (read sequence at the 5' end and read sequence at the 3' end) of each sample DNA fragment to provide the sequence data analyzer 1 with the result.

Additionally, it is a common notation for read sequences (base sequences) to describe base characters at the 5' end on the left side and describe base characters at the 3' end on the right side, thus hereinafter the 5' end is represented as "left", and the 3' end is represented as "right".

The sequencer 9 is configured as a super parallel typed (so called a next generation typed) DNA sequencer so as to sequence in parallel multiple (for example 1 billion pieces of) sample DNA fragments.

Similarly, the genome server 8 provides the genome sequence obtained by sequencing a genome DNA with the sequence data analyzer 1.

Further, it is possible to detect splice variants by instead of using the genome sequence obtained sequencing a genome DNA for a reference sequence and analyzing sample DNA fragments, by using mRNA sequences for a reference sequence and analyzing the paired-end sequencing data of cDNA samples. This is because the loss of exons by splice variants corresponds to "deletion" of a structural mutation, and the incorporation of new exons corresponds to "insertion" of a structural mutation.

FIG. 2 is a configuration illustrating the sequence data analyzer 1. The outline of each component is described in FIG. 2, and the details of each component will be disclosed below.

The sequence data analyzer 1 receives the inputs of read sequence group (a left sequence 11a and a right sequence 11b) from the sequencer 9.

The read sequence group 11 is a group of the read sequences (the left sequence 11a and the right sequence 11b) obtained from each sample DNA fragment sequenced by the sequencer 9.

The left sequence 11a is a read sequence obtained by sequencing toward the 3' end from the endpoint at the 5' end as a base point of a sample DNA fragment The right sequence 11b is a read sequence obtained by sequencing toward the 5' end with the endpoint at the 3' end as a base point of a sample DNA fragment.

Here, the lengths of the left sequence 11a and the right sequence 11b are approximately, for example, 100 bases, and assuming the length of a sample DNA fragment is approximately 300 bases, approximately 100 bases in the center, which are included neither in the left sequence 11a nor the right sequence 11b, are parts excluded from sequencing. Alternatively, a sample DNA fragment having a length of around 20 thousand bases includes around 19800 bases of the positions excluded from sequencing.

A read dictionary preparation unit 21 prepares the read sequence dictionary 14 from the read sequence group 11 for the preparation before DNA analysis processing. A genome dictionary preparation unit 22 prepares the genome sequence dictionary 15 from a reference genome sequence 12.

Additionally, the reference genome sequence 12, which is determined in advance for each species to be analyzed, is a group of sequences in a full length of each of the chromosomes.

The sequence analyzer 1 receives the inputs of SNP information 13a or structural mutation information 13b as the analysis information for indicating the mutation to be analyzed this time. SNP means that the base at a certain position of a sample DNA fragment differs from the base at the same position of a genome DNA. A structural mutation means insertion and deletion of a plurality of continuous bases alignment.

A query creation unit 23 creates a query sequence 16 including the mutation indicated by the analysis information 13 with reference to the genome sequence dictionary.

The query retrieval unit 24 retrieves a hit position 17a which is a base position coordinate to be mapped on the query sequence 16 (the query sequence 16 appears) from the read sequence dictionary 14.

A sample reconstruction unit 25 reconstructs read sequences (sample sequences 17) of a sample DNA fragment including the hit position 17a. Here, the hit position 17a is included either in the left sequence 11a or in the right sequence 11b, thus one of the read sequences in which the hit position 17a is not included is designated as a mate sequence 17b.

A mapping unit 26 refers to the genome sequence dictionary 15 to specify (genome mapping) in a genome DNA a position from which the mate sequence 17b of the sample DNA fragment is derived.

A sample determination unit 27 determines whether the sample DNA fragment of the mate sequence 17a includes the mutation indicated by the analysis information 13 according to success or failure in mapping of the mate sequence 17b. Further, the sample determination unit 27 outputs the determination result of analysis information 13.

Figure 3:
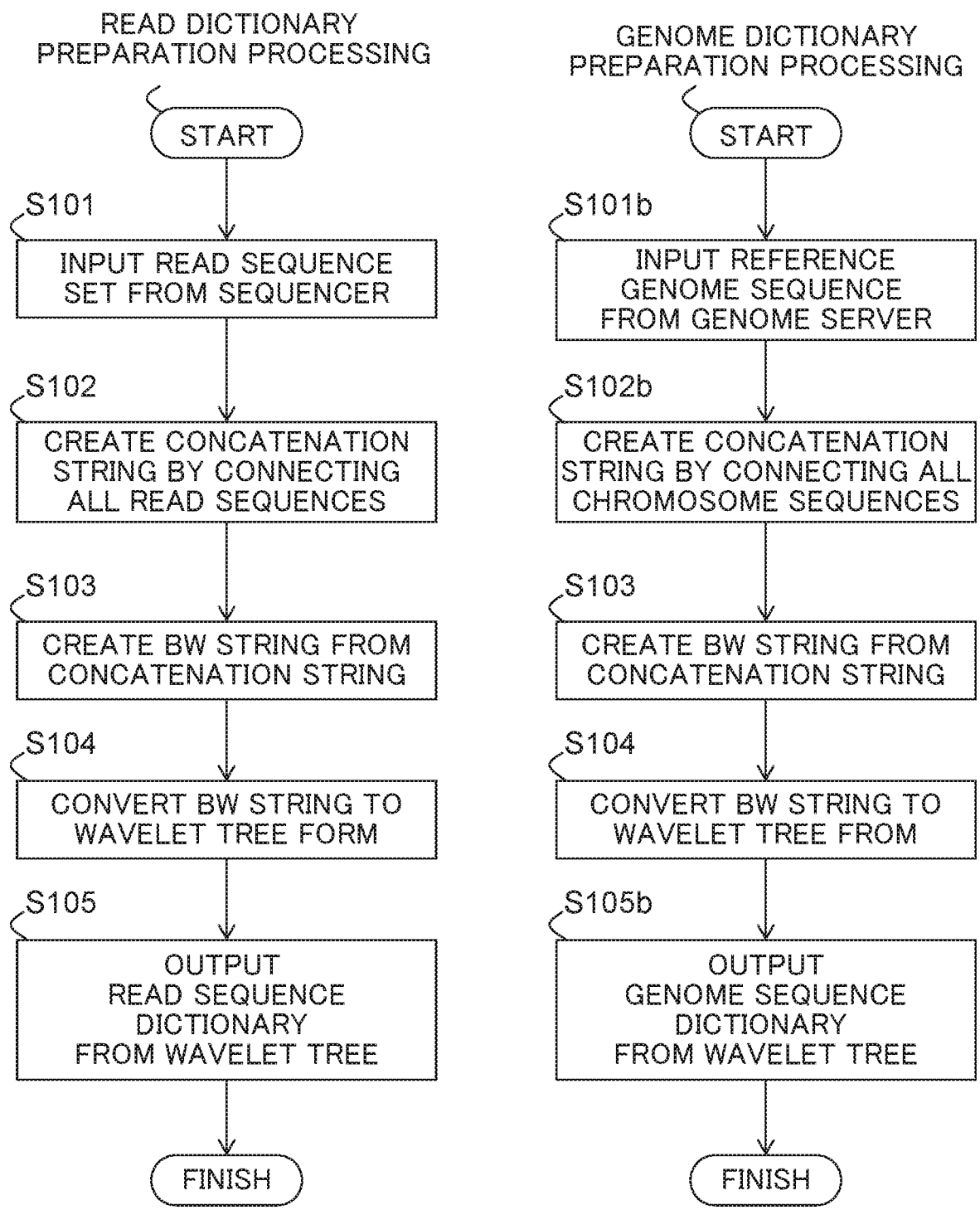
FIG. 3 is a flowchart showing a processing of creating each dictionary according to an embodiment of the present invention FIG. 4 are explanatory drawings illustrating a processing of creating a BW string in processing of creating dictionary according to an embodiment of the present invention.

FIG. 3 shows flowcharts describing the creating processing of each dictionary. Firstly, the read dictionary creation steps (S101-S105) where the read dictionary preparation unit 21 prepares the read sequence dictionary 14 from the read sequence group 11 will be described.

In S101, the sequence data analyzer 1 receives the inputs of read sequence group 11 (the left sequence 11a and the right sequence 11b) from the sequencer 9.

Figure 4A:
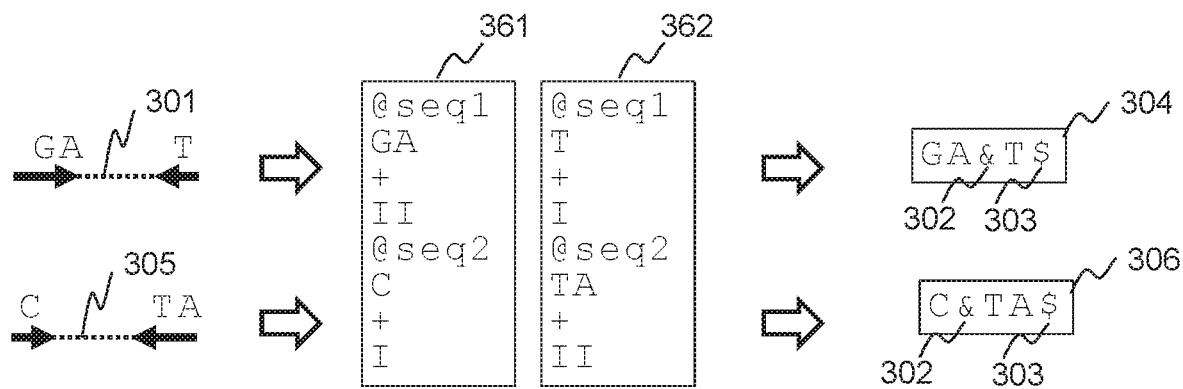
FIG. 4A illustrates a processing of creating concatenation strings from read sequences.

To provide an easy understanding with FIG. 4A, two pieces of sample DNA fragments 301 and 305 are illustrated, and in the sample DNA fragment 301 "GA" on the left sequence 11a is counted as 2 bases and "T" on the right sequence 11b is counted as 1 base, while in the sample DNA fragment 305 "C" on the left sequence 11a is counted as 1 base and "TA" on the right sequence 11b is counted as 2 bases.

The sequencer 9 notifies the sequence data analyzer 1 of the read sequence group 11 obtained by sequencing in FASTQ format as a sign 361 indicating the left sequence 11a and a sign 362 indicating the right sequence 11b. The read sequences of 2 sample DNA fragments are listed in the sign 361 and the sign 362 respectively, in which 4 lines of information are described on 1 read sequence.

The first line "@seq1, @seq2" in FASTQ format represents an identifier (ID) of a sample DNA fragment, and the second line "GA, T, C, TA" represents a read sequence. For example, the correspondence between the first line "@seq1" of the sign 361 and the first line "seq1" of the sign 362 prove to be a pair obtained by sequencing the same sample DNA fragment 301.

In S102 in FIG. 3, the read dictionary preparation unit 21 concatenates with a concatenation character "&" the base characters of a pair of the left sequence and the right sequence so as to create a concatenation string indicating a piece of a sample DNA fragment. Additionally, the base characters are "A, C, G, T" to represent 4 kinds of bases respectively and "N" to represent an unknown base.

In FIG. 4A, a pair of the left sequence 11a "GA" and the right sequence 11b "T" of the same sample DNA fragment 301 are concatenated with a concatenation character "&" 302, and added by a terminal character "$" 303 to the end, so that a concatenation string 304 "A&T$" is obtained. Likewise, a concatenation string 306 "C&TA$" is obtained from a pair of the sample DNA fragment 305.

Further, a plurality of different kinds of concatenation characters may be used according to the lengths of sample DNA fragments. For example, "&" may be used for a concatenation character in the concatenation string generated from approximately 300 bases of a sample DNA fragment composed of bases, while "#" may be used for a concatenation character in the concatenation string generated from approximately 20000 bases of a sample DNA fragment. This makes it possible to obtain not only a pairing partner of a sample DNA fragment but also a length of a sample DNA fragment from concatenation characters.

In S103 in FIG. 3, the read dictionary preparation unit 21 performs BW transformation on the concatenation strings 304 and 306 to create a BW string 311.

Figure 4B:
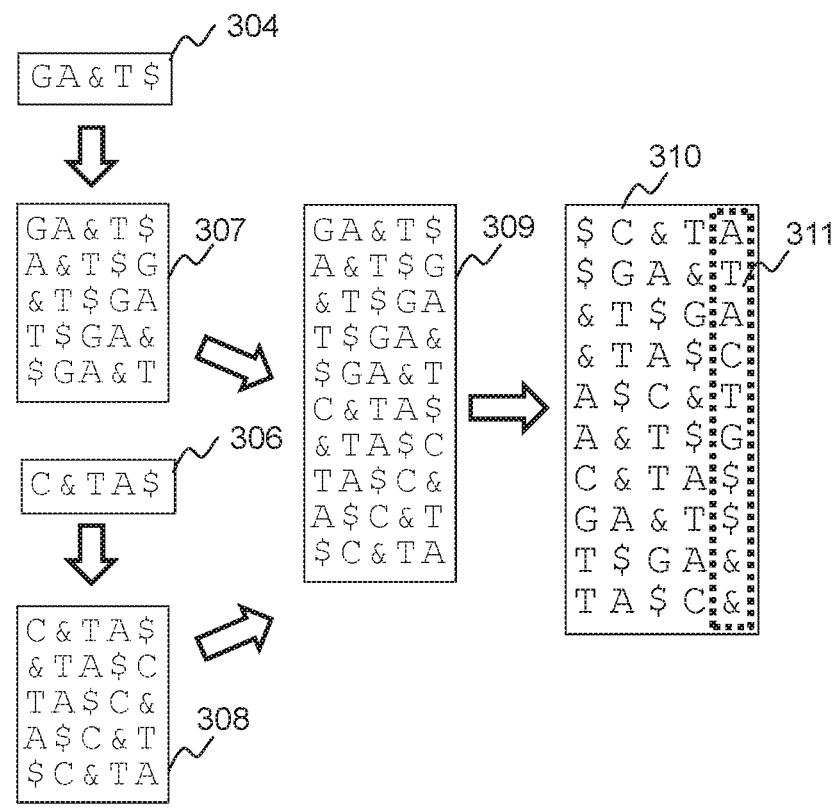
FIG. 4B illustrates a processing of creating BW strings from concatenation strings.

In FIG. 4B, the BW string 311 is created, for example, by the following procedure. In this computing process, when a comparison is made between a character from the concatenation string 304 and a character from the concatenation string 306 sequentially from the head, when a comparison is made between "$" from the concatenation string 304 and "$" from the concatenation string 306, a comparison is terminated, and when a comparison is made between "&" from the concatenation string 304 and "&" from the concatenation string 306 is compared with each other, a comparison is continued.

(Process 1) A string list 307 is obtained by performing a cyclic shift of the concatenation string 304, and a string list 308 is obtained by performing a cyclic shift of the concatenation string 306.

(Process 2) A merged list 309 is obtained by merging 2 lists of 307 and 308.

(Process 3) A sorted list 310 is obtained by sorting the merged list 309 in alphabetical order. The sorting rank of characters is, for example, "$<#<&<A<C<G<T<N" in this case.

(Process 4) A BW string 311 is formed by concatenating the end characters of each line of the sorted list 310.

Since the BW string 311 thus obtained has already been sorted, the same characters frequently continues. However, the data amount can be compressed by performing a run length encoding on the BW string 311.

In S105 in FIG. 3, the read dictionary preparation unit 21 converts the BW string 311 into Wavelet Tree format to prepare the read sequence dictionary 14 for efficient retrieval.

Figure 5A:
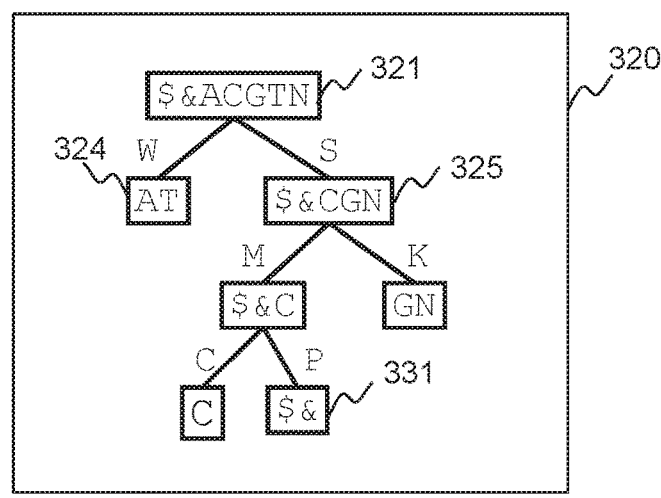
FIG. 5A illustrates the binary tree which is referred to for converting to Wavelet Tree form.

FIG. 5A illustrates a binary tree 320 which is referred to for converting the BW string 311 into Wavelet Tree format. This binary tree 320 designates all of characters ($, &, A, C, G, T, N) 321 used for the string as a root node.

The binary tree 320 describes the division method of dividing recursively all the characters ($, &, A, C, G, T, N) 321 used for the string into 2 groups so as to include at most 2 kinds of characters at the terminal of the division.

At the root node of the binary tree 320, all the characters 321 are divided into A, T (W) 24, and the others (S) 325. The characters ($, &, C, G, N) 3250 divided into S are similarly divided into M and K. This is repeated recursively until at most 2 kinds of characters are included at the terminal of the division. However, the sign "&" 302 indicating a pair and the terminal sign "$" 303 are divided so as to appear together at a terminal 331 of the division.

Figure 5B:
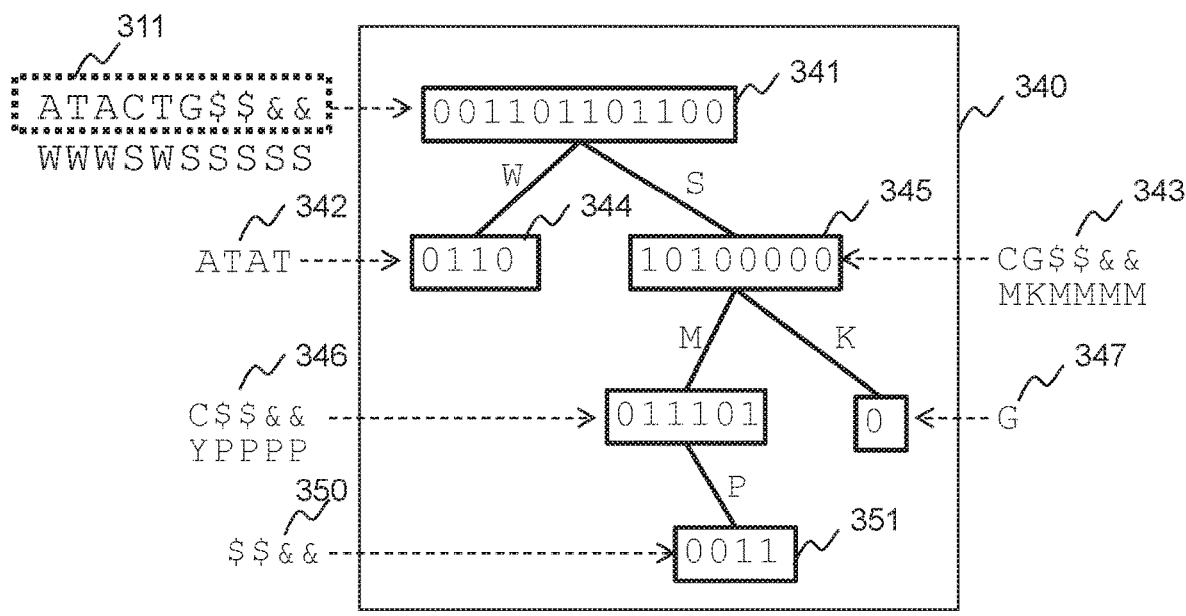
FIG. 5B illustrates the conversion processing of converting a BW string to Wavelet Tree form.

A wavelet Tree 340 in FIG. 5B is a binary tree indicating the BW string 311. The root node of the Wavelet Tree 340 is obtained by transforming the BW string 311 into a binary string 341 according to two groups of W and S in the binary tree 320. The read dictionary preparation unit 21 creates a partial string 342 formed by extracting the characters divided into W and a partial string 343 formed by extracting the characters divided into S.

The read dictionary preparation unit 21 converts the partial string 342 (including only 2 kinds of characters A and T) into a binary string 344 consisting of 0 and 1.

The read dictionary preparation unit 21 similarly converts the partial string 343 into a binary string 345 according to two groups of M and K formed by characters divided into S (indicated by the binary tree 320).

The read dictionary preparation unit 21 creates a partial string 346 formed by extracting the characters divided into M and a partial string 347 formed by extracting the characters divided into K.

By repeating the processing of creating each partial string as described above, 6 pieces of binary strings are formed as illustrated. At a terminal 351 of the division, a string 350 consisting of the sign "&" 302 indicating a pair and the terminal sign "$" 303 is represented by a binary string 351. The length (the number of bits) of the binary string 351 is equal to the total number of reads (2 times the total number of pairs).

Consequently, the wavelet tree 340 is obtained by performing an invertible transformation on the BW string 311, thus the BW string 311 can be reconstructed from the Wavelet Tree 340.

In S106 in FIG. 3, the read dictionary preparation unit 21 outputs the read sequence dictionary 14 created from the Wavelet Tree 340 to a storage unit. Here, the read dictionary preparation unit 21 may add to the read sequence dictionary 14 besides the Wavelet Tree 340 a small (approximately 3.5% data amount relative to the BW string 311) auxiliary data for computing a rank function and a select function of the Wavelet Tree 340.

Rank (p, c) is a function returning a number of appearances of a character "c" out of sequence elements 0 to p.

Select (i, c) is a function returning a sequence position at which the (i+1)th character "c" appears.

Auxiliary data is a "hierarchical binary string" described, for example, in a reference literature "Kouichi Kimura, Yutaka Suzuki, Sumio Sugano, and Asako Koike, Computation of Rank and Select Functions on Hierarchical Binary String and Its Application to Genome Mapping Problems for Short-Read DNA Sequences, Journal of Computational Biology, November 2009, 16(11): 1601-1613". This auxiliary data is used for efficiently performing retrieval mainly of all the read sequence fragments corresponding to a base sequence arbitrary selected from the BW string 311.

Since the auxiliary data used for calculating efficiently a rank function and a select function are is provided on the string obtained by BW transformation, it is possible to find out efficiently all the read sequence fragments corresponding to a string s arbitrary selected and further to perform reconstruction computing of the left and right sequences (, each of which extends up to "$") obtained from each read sequence fragment by using the characteristics of BW transformation that two kinds of separators $ and & are used.

Read dictionary preparation steps (S101 to S105) have been described as above with reference to FIG. 3 to FIG. 5. Meanwhile, genome dictionary preparation steps (S101b to S105b in FIG. 3) can be created similarly as the read dictionary creation steps (S101 to S105).

In S101b, the genome dictionary preparation unit 22 receives the inputs from the reference genome sequence 12 instead of the read sequence group 11 in S101.

In S102b, the genome dictionary preparation unit 22 concatenates a plurality of chromosome sequences (base strings) of a genome DNA represented by the reference genome sequence 12 as they are with the terminal character "S" to create a piece of string. Here, since the reference genome sequence 12 is not in a paired form, the pair concatenation processing with the concatenation character "&" shown as in S102 is not required.

In S105b, the genome dictionary preparation unit 22 outputs the genome sequence dictionary 15 instead of the read sequence dictionary 14 in S105.

Figure 6:
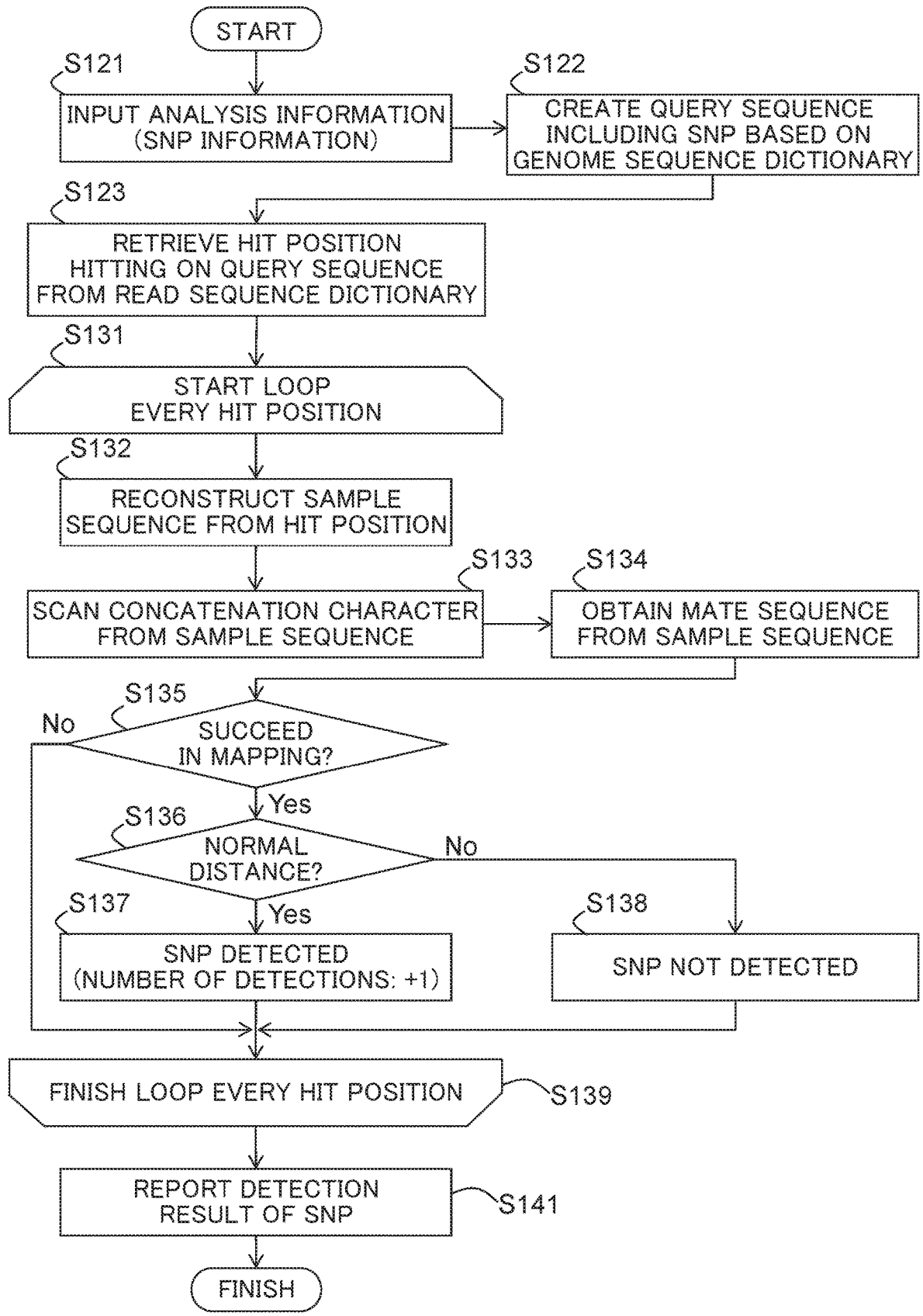
FIG. 6 is a flowchart showing SNP analysis processing according to an embodiment of the present invention.

FIG. 6 is a flowchart illustrating the analysis processing of SNP.

In S121, the sequence data analyzer 1 receives the inputs of the SNP information 13a as the analysis information 13 representing the mutation to be analyzed this time.

FIG. 7A illustrates a table 400 showing the SNP information 13a. As shown in each line of the table 400, each SNP includes the information of a chromosome name, a base position coordinate on a chromosome, a kind of base in the reference genome sequence (normal base), and a kind of base appearing as SNP (mutated base).

The first line of the table 400 shows that SNP is positioned in the 123456th base on a chromosome 7 and a base "A" of the reference genome is mutated to a base "G".

In S122 in FIG. 6, the query creation unit 23 creates the query sequence 16 including SNP indicated by the SNP information 13*a* with reference to the genome sequence dictionary 15.

A description field 420 in FIG. 7B illustrates S122, in which a horizontal axis 421 indicates a base position coordinate on a chromosome. Firstly, the query creation unit 23 refers to the genome sequence dictionary to find out a base sequence 422 in the string of (for example, approximately 10 bases leftward and rightward) a SNP position 424 shown in the first line in the table 400. The query creation unit 23 mutates the bases of the base sequence 422 at the SNP position 424 to create a sequence 423, which is designated as the query sequence 16. Alternatively, the query creation unit 23 designates the base sequence not including a mutation as the query sequence 16 instead of the base sequence 423 including a mutation so as to detect a normal base appearing at the SNP position 424.

In S123 in FIG. 6, the query retrieval unit 24 retrieves the hit position 17*a* which is a base position coordinate from within the read sequence dictionary 14 to be mapped on the query sequence 16 (the alignments of the base strings are corresponding).

Additionally, in the computing process based on the read sequence dictionary 14 converted by BW transformation, when a comparison is made between a character from the read sequence dictionary 14 and a character from the query sequence 16 sequentially from the heads, if "$" from the read sequence dictionary 14 and "$" from the query sequence 16 are compared with each other, a comparison is terminated, and if "&" from the read sequence dictionary 14 and "&" from the query sequence 16 are compared with each other, a comparison is continued.

In S131 to S139, the sequence data analyzer 1 executes loop processing on each of the hit positions 17*a* which have been found out in S123.

In S132, the sample reconstruction unit 25 reconstructs the read sequence (the sample sequence 17) of the sample DNA fragment including the hit position 17*a* currently selected in the loop from S131. In this reconstruction processing, the read sequence dictionary 14 created by BW transformation is scanned by extending from the hit position 17*a* up to the terminal character "$" by using a rank function and a select function, so that the sample sequence 17 between the left and right terminal characters "$" is obtained.

Such a method of using a rank function and a select function is described in, for example, a reference "Ferragina, P. and Manzini, G, Opportunistic data structures with applications, In 41$^{st}$ IEEE Symposium on Foundations of Computer Science, FOCS, pages 390-398".

The sample sequence 17 includes the concatenation character "&" and the terminal character "$" as the concatenation strings 304 and 306. This sample sequence 17 is separated by the concatenation character "&", so that a pair of two read sequences (the left sequence 11*a*, the right sequence 11*b*) are obtained without using an identifier for each sample DNA fragment.

In S133, the sample reconstruction unit 25 scans (inspects) the sample sequence 17 up to the concatenation character "&" as described below so as to obtain the mate sequence 17*b*(S134).

In the case of [1] in FIG. 7C, since the concatenation character "&" appears in the sequence extending rightward from the sequence 423 at the hit position 17*a*, the obtained mate sequence 17*b* is the right sequence 11*b* extending on the right side of the concatenation character "&".

In the case of [2] in FIG. C, since the concatenation character "&" doesn't appear in any sequence extending rightward or leftward from the sequence 423 at the hit position 17*a*, the obtained mate sequence 17*b* is the left sequence 17*b* extending on the left side of the concatenation character "&".

In the case of [3] in FIG. C, if the concatenation character "&" appears by extending neither rightward nor leftward from the sequence 423 at the hit position 17*a*, the sample sequence 17 is an independent read sequence without a partner constituting a pair. Such an independent read sequence may be considered as unreliable to be ignored.

Alternatively, only if it is confirmed there is only one position at which the sequence 423 appears in a genome by inquiring the genome dictionary for the sequence 423 before introducing a mutation, it may be determined that SNP was detected (though unreliable).

In S 135, the mapping unit 26 refers to the genome sequence dictionary so as to specify (genome mapping) in the genome DNA the position from which the mate sequence 17*b* obtained in S134 is derived. The mapping unit 26, for example, cuts out a short partial sequence (for example, approximately bases) from the mate sequence 17*b* and inquires the genome dictionary 15 for whether the partial sequence appears only at one position in the genome.

If the partial sequence doesn't appear even at any position, it is assumed that the partial sequence includes a sequence error or polymorphism, thus the mapping unit 26 inquires the genome dictionary 15 for another partial sequence again.

Further, if the partial sequence appears in a plurality of positions, the mapping unit 26 inquires the partial sequence in an increased length or another partial sequence again. When the position of the short partial sequence is thus specified at a genome, the position of the mate sequence 17*b* including the short partial sequence can also be specified at the genome (it other words, succeed in mapping). On the other hand, when the position cannot be specified, the mapping unit 26 fails in mapping.

When the determination of S135 becomes Yes, the loop advances to S136, while when the determination of S135 becomes No, this loop terminates (S139) to return to S131 for selecting the next hit position.

In S136, the sample determination unit 27 determines whether the sample DNA fragment of the sequence 17*a* in S132 includes SNP mutation indicated by the analysis information 13 depending on whether the distance is normal (matching) or not as described below. For example, the sample determination unit 27, when the distance between the mapping position of the mate sequence 17*b* having succeeded in mapping and the SNP position indicated by the SNP information 13*a* (the hit position 17*a*) is approximately equal to the length of the sample DNA fragment, considers that the left sequence 11*a* and the right sequence 11*b* constituting the sample sequence 17 are matched to be determined as "SNP detected" (in other words, matching to the SNP information 13*a*).

When the determination of S136 becomes Yes, the loop advances to S137, while when the determination of S136 becomes No, the loop advances to S138.

In S137, the sample determination unit 27 increases the detection number counter value of the SNP information 13a determined as "SNP detected" by one.

In S138, the sample determination unit 27 doesn't increase the detection number counter value due to the determination as "SNP undetected".

In running the loop from S131 to S139, in S141 the sample determination unit 27 outputs (reports to a user) the determination result of the analysis information 13 having associated the SNP information 13a with the detection number counter value (the number of the sample DNA fragments in which SNP is detected).

A table 460 in FIG. 7D is one example of information output in S141. The number of read fragments (mutated base detection number) in which a mutated base (SNP) is detected in the SNP position 424 and the number of read fragments (normal base detection number) in which a normal base is detected for each SNP shown in the table 400 in FIG. 7A are read from the detection number counter value and written in the table 460.

Figure 8:
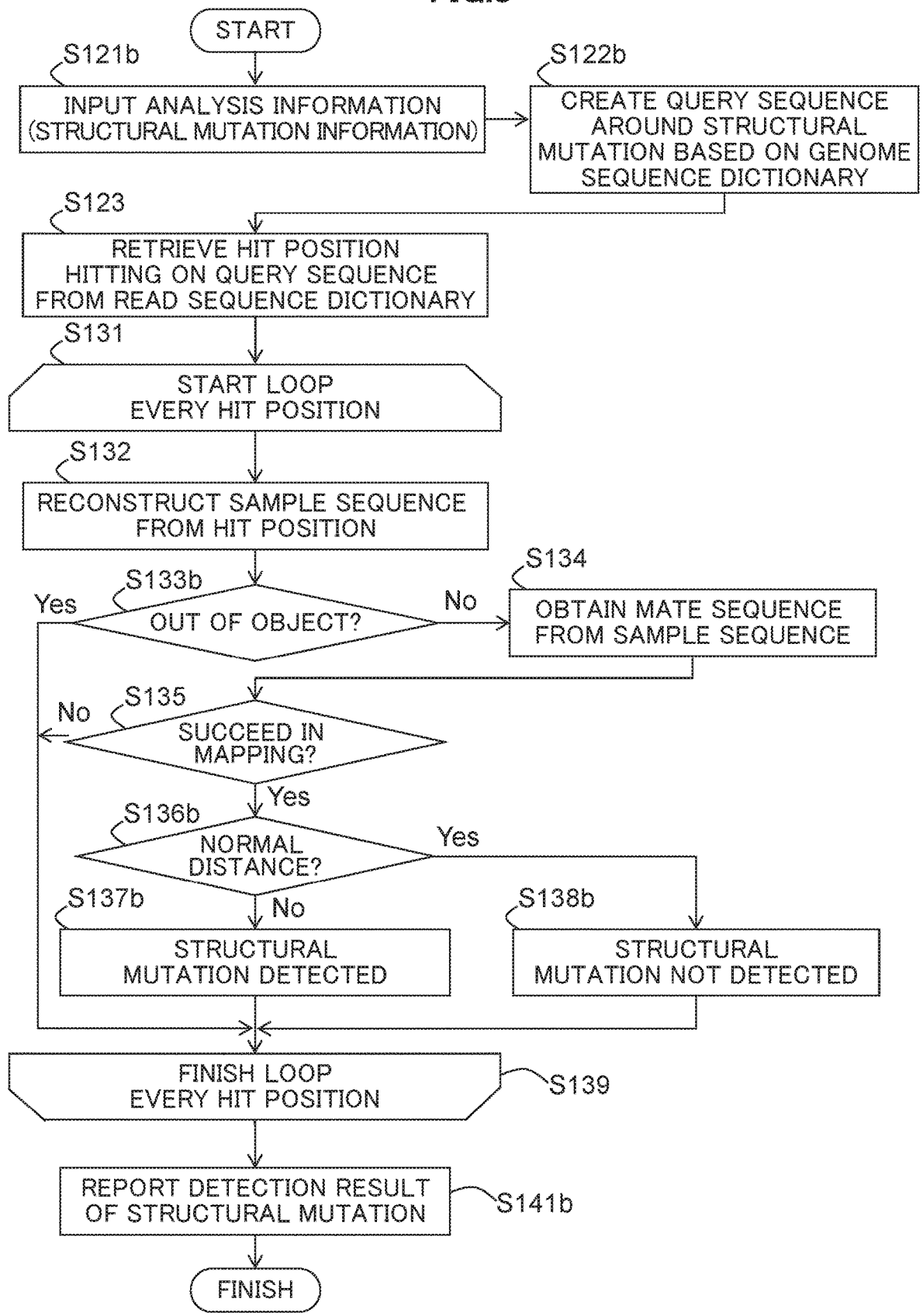
FIG. 8 is a flowchart showing the analysis processing of the structural mutation according to an embodiment of the present invention.

FIG. 8 is the flowchart indicating analysis processing of structural mutation. FIG. 8 will be described in the following by focusing on the difference with analysis processing of SNP in FIG. 6.

In S121b, the sequence data analyzer 1 receives the input of structural mutation information 13b instead of the SNP information 13a as the analysis information 13 indicating the mutation to be analyzed this time.

The structural mutation information 13b in FIG. 9A includes a chromosome name, a base position coordinate on a chromosome, a mutation type (insertion or deletion), and information on a mutation length shown in each line of a table 600.

The first line of the table 600 indicates that a structural mutation is in the position of the 654321th base on the third chromosome and that the deletion in which the alignment of 500 continuous bases is lost from the normal genome is caused.

In S122b in FIG. 8, the query creation unit 23 creates the query sequence 16 in the string of a structural mutation indicated by the structural mutation information 13b with reference to the genome sequence dictionary 15.

A description field 620 in FIG. 9B illustrates the creation method of the query sequence 16 in S122b is described. The horizontal axis 421 indicates a base position coordinate on a chromosome. Firstly, with reference to the genome sequence dictionary 15, short (for example, approximately 20 bases) base sequences 622 and 623 in the string (for example, in the position tens of bases away leftward and rightward) of the position 624 in which a structural mutation is caused are found out to be designated as the query sequence 16 respectively. Namely, the query sequence 16 is a short sequence in the string (leftward or rightward) of the position 624 in which a structural mutation is caused.

In S133b in FIG. 8, after executing a processing of S133 (not shown in FIG. 8), it is determined whether the concatenation string of the sample sequence reconstructed from the hit position is excluded from structural mutation analysis (mutation information is not obtained) or not. When the determination of S133b becomes Yes, this loop terminates (S139), while when the determination of S133b becomes No, this loop advances to S134. The determination processing of S133b will be described hereinafter with reference to the description field 640 of FIG. 9C.

As in the case of [1] in FIG. 9C, where the concatenation character "&" appears in the sample sequence 17 reconstructed in such a way that the query sequence 622 on the left of the position 624 being the hit position 17a extends rightward, the query sequence 622 is included in the left sequence 11a.

Consequently, the sequence 641 (the right sequence 11b) on the right of the concatenation character "&" is reconstructed as the mate sequence 17b. Further, the position 624 in which a structural mutation is caused can be included between the query sequence 622 and the sequence 641.

On the other hand, though not shown in FIG. 9C, when the concatenation character "&" appears in a string which is reconstructed in such a way that the query sequence 622 extends leftward, there is to no possibility of a structural mutation, thus it is determined as out of an object (mutation information is not obtained).

As in the case of [2] in FIG. 9(c), the similar determination is performed on the query sequence 623 toward the right of the position 624 being the hit position 17a by flipping horizontally [1] in FIG. 9 C. When the concatenation character "&" appears in the sample sequence 17 reconstructed in such a way that the query sequence 623 extends leftward, the query sequence 623 is included in the right sequence 11b.

Consequently, the sequence 642 (the left sequence 11a) extending leftward from the concatenation character "&" is reconstructed as the mate sequence 17b. Further, the position 624 at which a structural mutation is caused is likely to be included between the query sequence 623 and the sequence 642.

On the other hand, though not shown in FIG. 9C, when the concatenation character "&" appears in the sequence reconstructed in such a way the query sequence 623 extends rightward, there is to no possibility of a structural mutation, thus it is determined as out of an object (mutation information is not obtained).

The above describes the determination processing of S133b.

In S136b performed instead of S136, when the distance of the pair of read sequences between the mate sequence 17b and the sample sequence 17 from which the mate sequence 17b is extracted is almost equal to the length of sample DNA fragments, the sample determination unit 27 evaluates that the distance is a normal value (S136b, Yes).

When the determination of S136b becomes No, a structural mutation is detected, thus the sample determination unit 27 increases the counter value of "the number of mutations detected" of the corresponding structural mutation information 13b by one.

Here, the sample determination unit 27 may total the number of detection separately for a mutation type "deletion" and a mutation type "insertion". Therefore, when a distance between a pair is longer than predicted by a length of sample DNA fragment, it may be determined that deletion (corresponding to a length of the difference) is caused, to the contrary, when a distance between a pair is shorter than predicted by a lengths of a sample DNA fragment, it may be determined that insertion (corresponding to a length of the difference) is caused.

When the determination of S136b becomes Yes, a structural mutation is not detected, thus the sample determination unit 27 increases the counter value of "the number of mutations undetected" of the corresponding structural mutation information 13b by one (S138b).

In S141b, the sequence data analyzer 1 reports the counter values of S137b and S138b as the detection results of structural mutations, so that the information shown by a table 660 of FIG. 9D is output.

The table 660 reports, for each structural mutation shown in the table 600, the number of read fragments determined as existence of a mutation and the number of read fragments determined as non existence of a mutation (in other words, corresponding to a normal genome) as the number of detecting existence of mutations and the number of detecting nonexistence of mutations respectively.

In the embodiment described above, the read dictionary preparation unit 21 connects the left sequence 11*a* and the right sequence 11*b* which constitutes a pair of a sample DNA fragment with the concatenation character and connects pairs of each of the sample DNA fragments with the terminal characters so as to create a concatenation string. And, the read dictionary preparation unit 21 performs a BW transformation on the concatenation string, and then prepares the read sequence dictionary 14 formatted as Wavelet Tree.

The sample reconstruction unit 25, when reconstructing the pairing partner (the mate sequence 17*b*) of the sample DNA fragment including the hit position 17*a* from the hit position 17*a* of the query sequence 16 in the read sequence dictionary 14, can reconstruct the mate sequence 17*b* based on the concatenation character embedded in the read sequence dictionary 14. Accordingly, the identifier for each sample DNA fragment is not required, so that the mate sequence 17*b* constituting a pair for any read sequence can be efficiently computed.

Additionally, the amount of data and processing to be dealt with by the sequence data analyzer 1 can be reduced by not using an identifier for each sample DNA fragment as described below.

As a comparative example, when an identifier for each sample DNA fragment as "@seq1" indicated by a sign 361 in FIG. 4 is used, if the read sequence group 11 read from a sample DNA fragment consists of 1 billion of the left sequence 11*a* and the right sequence 11*b*, 5 billion kinds of identifiers are required. Assuming that the data size of one identifier is 4-byte, the data size of all identifiers requires 4-gigabyte. Further, when the identifier for each sample DNA fragment is used, it is necessary to retrieve the mate sequence 17*b* constituting the pair with the identifier for the hit read sequence as a retrieval key.

On the other hand, in the embodiment, since the data size of the control characters (concatenation character, terminal character) embedded in the read sequence dictionary 14 is 1 bit for one sample DNA fragment, the total data size of all sample DNA fragments is 1 billion bit (equals to 0.125-gigabyte), which is approximately 32 times less than the data size in the case of using identifiers. Further, since the hit read sequence and the mate sequence 17*b* constituting the pair are aligned adjacently across the concatenation character in the read sequence dictionary 14, the retrieval load of the mate sequence 17*b* can be suppressed.

Furthermore, the present invention is not restricted to the above embodiment, but including various variations. For example, the above embodiment is a detailed explanation for describing easily the present invention, and not necessarily restricted to the embodiment having all configurations described.

Further, it is possible to replace some configurations of one embodiment with configurations of another embodiment, and it is also possible to add configurations of another embodiment to configurations of one embodiment.

Furthermore, it is possible to perform addition, deletion, replacement of other configurations for some configurations of each embodiment. Here, the part or all of each configuration, function, processing unit, and processing means as above may be designed by, for example, Integrated Circuit so as to be implemented in hardware.

Additionally, each of the configuration and function as above may be implemented in software in such a way a processor interprets and executes the program realizing each function.

The information such as program, table, and file for realizing each function can be stored in recording devices such as a memory, a hard disk, and a SSD (Solid State Drive) or recording mediums such as an IC (Integrated Circuit) card, a SD card, a DVD (Digital Versatile Disc).

Further, control lines and information lines which are necessary for the explanation are indicated, thus all control lines and information lines for the product are not necessarily indicated. It may be regarded that almost all the configurations are actually connected with each other.

REFERENCE SIGNS LIST 1 sequence data analyzer
8 genome server
9 sequencer
11 read sequence group
11*a* left sequence
11*b* right sequence
12 reference genome sequence
13 analysis information
13*a* SNP information
13*b* structural mutation information
14 read sequence dictionary
15 genome sequence dictionary
16 query sequence
17 sample sequence
17*a* hit position
17*b* mate sequence
21 read dictionary preparation unit
22 genome dictionary preparation unit
23 query creation unit
23 query retrieval unit
25 sample reconstruction unit
26 mapping unit
27 sample determination unit

What is claimed is:

1. A sequence data analyzer comprising:
a read dictionary preparation unit configured to prepare a read sequence dictionary based on billions of sample DNA fragments;
a temporary storage unit configured to temporarily store billions of strings prepared by the read dictionary preparation unit and used for preparing the read sequence dictionary, each of the strings consisting of a pair of a left sequence and a right sequence obtained by sequencing each sample DNA fragment from both ends thereof, a concatenation character connecting the left sequence and the right sequence without a sample DNA fragment identifier to obtain a concatenation string, and a terminal character connected to the concatenation string;
a query retrieval unit configured to search the read sequence dictionary for a hit position being a base character coordinate at which a query sequence appears, the query sequence being generated from a base string of a genome DNA;
a sample reconstruction unit configured to extract as a sample sequence a string having the hit position by searching the read sequence dictionary from the hit position up to a terminal character positioned around the hit position, to search the sample sequence for a concatenation character positioned around the hit position from the hit position up to the terminal character, and to extract as a mate sequence either one of the left sequence and the right sequence of the sample sequence, where the hit position does not exist; and a mapping unit configured to search the genome DNA for a base character coordinate of the base string in which the mate sequence appears.

2. The sequence data analyzer according to claim 1, further comprising:

a query creation unit configured to mutate a base character at a predetermined position among the base string of the genome DNA to a different base character to create the query sequence including the mutated base character and a base string of the genome DNA positioned at both ends of the mutated base character; and a sample determination unit configured to detect, when a base character coordinate of the mate sequence is specified by the mapping unit, Single Nucleotide Polymorphism (SNP) in the sample DNA fragment based on a length of the sample DNA fragment specified by a character interval of the base character coordinate between the hit position and the mate sequence.

3. The sequence data analyzer according to claim 1, further comprising:

a query creation unit configured to create the query sequence from the base string of the genome DNA positioned in the string of a predetermined position among the base string of the genome DNA; and a sample determination unit configured to detect, when the base character coordinate of the mate sequence is specified by the mapping unit, a structural mutation in the sample DNA fragment based on a length of the sample DNA fragment specified by a character interval of the base character coordinate between the hit position and the mate sequence.

4. The sequence data analyzer according to claim 1, wherein the read dictionary preparation unit creates a Burrows-Wheeler (BW) string which is obtained by performing a BW transformation on the string obtained by connecting the concatenation strings of each of the sample DNA fragments with the terminal characters, and converts the BW string into Wavelet Tree format to prepare the read sequence dictionary.

5. The sequence data analyzer according to claim 1, wherein the read dictionary preparation unit creates the concatenation string by using a plurality of kinds of the concatenation characters corresponding to a length of each of the sample DNA fragments.

6. The sequence data analyzer according to claim 1, wherein the sample reconstruction unit excludes the hit position from objects to be processed by the mapping unit, when the concatenation character does not exist in the string of the hit position.

7. The sequence data analyzer according to claim 1, wherein data required for identifying the concatenation character and the terminal character is embedded in the read sequence dictionary for each of the sample DNA fragments.

8. The sequence data analyzer according to claim 7, wherein a size of the data for identifying the concatenation character and the terminal character is 1 bit.

9. The sequence data analyzer according to claim 1, further comprising a storage unit configured to store the read sequence dictionary.

10. A DNA analysis system comprising:

a sequence data analyzer according to claim 1; and a sequencer configured to sequence each of the sample DNA fragments from both ends thereof to obtain a pair of read sequences constituted of the left sequence and the right sequence, and to transmit the pair of read sequences to the sequence data analyzer.

11. A method of analyzing sequence data using billions of sample DNA fragments, the method comprising:

preparing billions of strings each consisting of a pair of a left sequence and a right sequence obtained by sequencing each sample DNA fragment from both ends thereof, a concatenation character connecting the left sequence and the right sequence without a sample DNA fragment identifier to obtain a concatenation string, and a terminal character connected to the concatenation string;

preparing a read sequence dictionary from the strings;

searching the read sequence dictionary for a hit position being a base character coordinate at which a query sequence appears, the query sequence being generated from a base string of a genome DNA;

searching the read sequence dictionary from the hit position up to a terminal character positioned around the hit position to extract as a sample sequence a string having the hit position;

searching the sample sequence for a concatenation character positioned around the hit position from the hit position up to the terminal character;

extracting as a mate sequence either one of the left sequence and the right sequence of the sample sequence, where the hit position does not exist; and searching the genome DNA for a base character coordinate of the base string in which the mate sequence appears.

12. The method according to claim 11, further comprising:

temporally storing the strings each consisting of the left sequence, the right sequence, the concatenation character connecting the left sequence and the right sequence, and the terminal character connected to the concatenation string;

creating a Burrows-Wheeler (BW) string which is obtained by performing a BW transformation on each of the strings; and converting the BW string into Wavelet Tree format to prepare the read sequence dictionary.

* * * * *